(12) United States Patent
Garcia et al.

(10) Patent No.: US 8,697,628 B2
(45) Date of Patent: Apr. 15, 2014

(54) METHODS OF USING AMPD2 INHIBITORS FOR THE TREATMENT OF FATTY LIVER, OBESITY AND DIABETES

(75) Inventors: Gabriela Garcia, Denver, CO (US); Richard J. Johnson, Centennial, CO (US); Christopher J. Rivard, Lakewood, CO (US); Miguel A. Lanaspa-Garcia, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 13/521,881

(22) PCT Filed: Jan. 13, 2011

(86) PCT No.: PCT/US2011/021220
§ 371 (c)(1),
(2), (4) Date: Jan. 11, 2013

(87) PCT Pub. No.: WO2011/088272
PCT Pub. Date: Jul. 21, 2011

(65) Prior Publication Data
US 2013/0209484 A1    Aug. 15, 2013

Related U.S. Application Data

(60) Provisional application No. 61/294,581, filed on Jan. 13, 2010, provisional application No. 61/295,668, filed on Jan. 15, 2010, provisional application No. 61/297,944, filed on Jan. 25, 2010.

(51) Int. Cl.
*A01N 61/00* (2006.01)
*A61K 38/00* (2006.01)
*A61K 39/395* (2006.01)
*A01N 43/04* (2006.01)
*A61K 31/70* (2006.01)
*C12N 15/11* (2006.01)

(52) U.S. Cl.
USPC .............. 514/1; 424/158.1; 514/43; 514/44 A

(58) Field of Classification Search
None
See application file for complete search history.

(56) References Cited

PUBLICATIONS

Lanaspa MA, et al. PLOS ONE, 7:1-13, Nov. 2012.*
Shim. MS and Kwon YJ. Efficient and targeted delivery of siRNA in vivo. FEBS Journal, 277(23):4814-4827, Nov. 16, 2010 (online at—DOI: 10.1111/j.1742-4658.2010.07904.x).*

* cited by examiner

*Primary Examiner* — Robert Landsman
(74) *Attorney, Agent, or Firm* — Timothy H. Van Dyke; Beusse, Wolter, Sanks, Mora & Maire, P.A.

(57) ABSTRACT

The present invention provides compounds and compositions that modulate adenosine monophosphate deaminase (AMPD) and methods for using the same to treat a clinical condition associated with the metabolic syndrome or a disease associated with the metabolic syndrome. In particular, the present invention provides a compound and a composition comprising a selective AMPD2 inhibitor and methods for using the same, for example, to treat a clinical condition associated with metabolic syndrome as well as diseases manifested by the metabolic syndrome.

6 Claims, 13 Drawing Sheets

METHODS OF USING AMPD2 INHIBITORS FOR THE TREATMENT OF FATTY LIVER, OBESITY AND DIABETES

RELATED APPLICATIONS

This application is a U.S. national stage filing of PCT/US11/21220 filed Jan. 13, 2011, which claims the benefit of U.S. Ser. No. 61/294,581 filed Jan. 13, 2010; U.S. Ser. No. 61/295,668 filed Jan. 15, 2010 and U.S. Ser. No. 61/297,944 filed Jan. 25, 2010, all of which are incorporated herein by reference in their entireties.

STATEMENT REGARDING FEDERALLY FUNDED RESEARCH

This invention was made with government support under grant number 1RC4DK090859-01 awarded by the National Institutes of Health. The government has certain rights in the invention.

FIELD OF THE INVENTION

The present invention relates to adenosine monophosphate deaminase (AMPD) modulators and methods for using the same to treat a clinical condition associated with the metabolic syndrome. In particular, methods of the invention relate to administering a compound or a composition comprising a selective AMPD2 inhibitor to treat a clinical condition associated with metabolic syndrome as well as diseases manifested by the metabolic syndrome. These diseases and clinical conditions include, but are not limited to, diabetes, kidney disease, cardiovascular disease, vascular disease, chronic heart failure, and metabolic syndromes such as fatty liver, obesity, etc.

BACKGROUND OF THE INVENTION

A combination of risk factors or clinical conditions that occur together more often than by a mere chance that results in cardiovascular disease and type 2 diabetes mellitus have become known as the "metabolic syndrome." These clinical conditions include, but are not limited to, raised blood pressure, dyslipidemia (raised triglycerides and lowered high-density lipoprotein cholesterol), raised fasting glucose, and central obesity.

Metabolic syndrome is frequently associated with or strongly suggests prognosis or predicts development of a constellation of co-morbidity including diabetes, hypertension, coronary artery disease, vascular disease, chronic heart failure and chronic kidney disease. Metabolic syndrome is also frequently described as the underlying cause of serious cardiorenal diseases such as hypertension, coronary artery disease, vascular disease, chronic heart failure and chronic kidney disease. In addition, metabolic syndrome can also cause organ fibrosis (e.g., heart, lung and kidney).

Therefore, there is a need for a therapeutic treatment of metabolic syndrome or clinical conditions associated with metabolic syndrome to ameliorate or prevent these diseases.

SUMMARY OF THE INVENTION

Some aspects of the invention provide methods for treating a clinical condition associated with metabolic syndrome in a subject comprising administering to the subject in need of such a treatment a therapeutically effective amount of a composition comprising an adenosine monophosphate deaminase 2 (AMPD2) inhibitor. In particular, AMPD2 inhibitor has a selectivity that is at least 10 times more selective for AMPD2 compared to its selectivity for adenosine deaminase. In some embodiments, the AMPD2 inhibitor is at least 100 times more selective for AMPD2 compared to its selectivity for the adenosine deaminase. Often the AMPD2 inhibitor is at least 1,000 times more selective for AMPD2 compared to its selectivity for the adenosine deaminase.

Yet in other embodiments, the selectivity of AMPD2 inhibitor for AMPD2 is at least 10 times higher compared to its selectivity for other AMPDs. Typically, the selectivity of AMPD2 inhibitor for AMPD2 is at least 100 times higher compared to its selectivity for other AMPDs. Often, the selectivity of AMPD2 inhibitor for AMPD2 is at least 1,000 times higher compared to its selectivity for other AMPDs.

Without being bound by any theory, by using an AMPD2 inhibitor that is selective for AMPD2, methods of the invention significantly reduce or completely avoid at least some of the undesired side-effects of other AMPD inhibitors in treating a clinical condition associated with metabolic syndrome.

Still in other embodiments, the clinical condition associated with metabolic syndrome comprises obesity, diabetes, fatty liver, systemic hypertension, pulmonary hypertension, systemic inflammation, insulin resistance, dyslipidemia, chronic renal disease, arteriolosclerosis, sleep apnea, stroke, coronary artery disease, or a combination thereof. In some instances, the clinical condition associated with fatty liver comprises nonalcoholic fatty liver disease, nonalcoholic fatty liver disease associated cirrhosis, or a combination thereof.

Yet in other embodiments, administration of the AMPD2 inhibitor reduces plasma triglycerides, raises high-density lipoprotein (HDL) cholesterol, reduces the progression of chronic kidney disease, reduces the progression of diabetic nephropathy, preserves pancreatic islet function, improves oxidative stress, improves vascular function, reverses microvascular disease, reduces progression of chronic heart failure, or a combination thereof.

In some embodiments, methods of the invention also include using a composition that also comprises a non-selective AMPD inhibitor, an AMPD1 inhibitor, an AMPD3 inhibitor, or a combination thereof.

Still in other embodiments, the composition can further comprise a xanthine oxidase inhibitor, a uricosuric agent, KHK inhibitor, metformin, thiazolidinediones, an ACE inhibitor, an angiotensin receptor blocker, a thiazide diuretic, an antioxidant, catechin, resveratol, a uric acid lowering compound, or a combination thereof.

Yet in some embodiments, the AMPD2 inhibitor inhibits expression of AMPD2 gene, enzymatic activity of AMPD2 enzyme, or a combination thereof. In some particular instances, the AMPD2 inhibitor comprises a siRNA that inhibits expression of AMPD2 gene, an AMPD2 antibody, an AMP analog that inhibits AMPD2, an inhibitor of AMPDX that inhibits AMPD2, carbocyclic coformycin or a derivative thereof, carbocyclic nebularine or a derivative thereof, deaminoformycin or a derivative thereof, a compound disclosed in U.S. Pat. Nos. 4,912,092 and 5,731,432 or a derivative thereof, or a combination thereof.

BRIEF DESCRIPTION OF THE DRAWINGS

FIG. 1A is a schematic illustration showing the effects of AMP deaminase on AMP metabolism 1B is a schematic illustration showing a role of AMP deaminase in fat storage and diabetes.

FIG. 5A also shows that silencing of AMPD2 resutls in increase in phosphorylated AMPK as well as stimulation of the protein level of enoyl CoA hydratase-1 (ECH1) which is involved in β-fatty acid oxidation.

DETAILED DESCRIPTION OF THE INVENTION

Figure 1A:
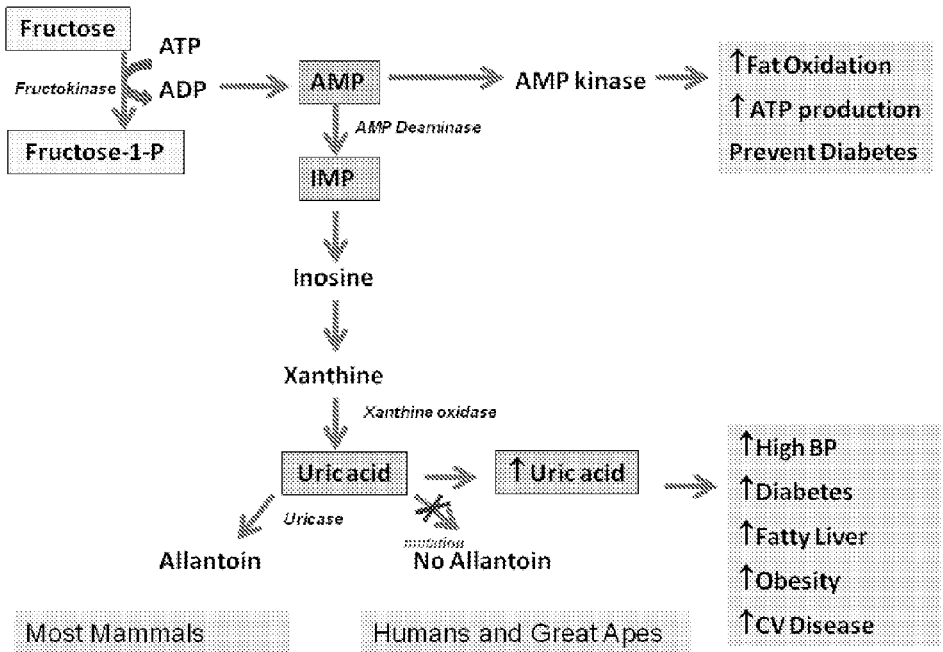
FIG. 1A-B.

As used herein, the term "inhibiting AMPD2" refers to reducing or preventing expression of AMPD2 gene, activity of AMPD2 enzyme, or a combination thereof.

As used herein, the term "treat", "treating" or "treatment" of a clinical condition, such as a clinical condition associated with the metabolic syndrome includes: (1) preventing the clinical condition, i.e., causing the clinical condition not to develop in a mammal; (2) inhibiting the clinical condition, i.e., arresting or reducing the development of the clinical condition; or (3) relieving the clinical condition, i.e., causing regression of the clinical condition.

A "metabolic syndrome" refers to risk factors for (or clinical conditions associated with increased likelihood of) developing cardiovascular disease (CVD) and/or diabetes. These factors include, but are not limited to, dysglycemia, raised blood pressure, elevated triglyceride levels, low high-density lipoprotein ("HDL") cholesterol levels, and obesity (particularly central adiposity). The clinical condition associated with metabolic syndrome is not an absolute risk indicator, because it does not contain many of the factors that determine absolute risk, for example, age, sex, cigarette smoking, and low-density lipoprotein ("LDL") cholesterol levels. Generally, patients with the clinical conditions associated with metabolic syndrome are at higher risk (e.g., at least twice likely) of developing CVD over the next 5 to 10 years as individuals without the clinical conditions associated with metabolic syndrome. Typically, the risk over a lifetime is even higher. In some cases, the metabolic syndrome confers a higher risk (e.g., at least 5-fold increase) for developing type 2 diabetes mellitus. Exemplary clinical conditions associated with metabolic syndrome include, but are not limited to, atherogenic dyslipidemia, elevated blood pressure, and elevated plasma glucose. Persons with these metabolic risk factors commonly manifest a prothrombotic state and a proinflammatory state. Atherogenic dyslipidemia consists of an aggregation of lipoprotein abnormalities that includes elevated serum triglyceride and apolipoprotein B, increased small low density lipoprotein particles, and a reduced level of high density lipoprotein cholesterol. Many persons with the metabolic syndrome have abdominal obesity and insulin resistance. Both of the latter conditions are believed to contribute to the development of other risk factors, although the mechanisms underlying these contributions are not fully understood. Some of the typical criteria for clinical diagnosis of the metabolic syndrome are listed in the table below:

| Table of Criteria for Clinical Diagnosis of the Metabolic Syndrome | |
|---|---|
| Measure | Categorical Cut Points |
| Elevated waist circumference | Population- and country-specific definitions |
| Elevated triglycerides (drug treatment for elevated triglycerides is an alternate indicator†) | ≥150 mg/dL (1.7 mmol/L) |
| Reduced HDL-C (drug treatment for reduced HDL-C is an alternate indicator†) | ≥40 mg/dL (1.0 mmol/L) in males; ≥50 mg/dL (1.3 mmol/L) females |
| Elevated blood pressure (antihypertensive drug treatment in a patient with a history of hypertension is an alternate indicator) | Systolic ≥130 and/or diastolic ≥85 mmHg |

-continued

Table of Criteria for Clinical Diagnosis of the Metabolic Syndrome

| Measure | Categorical Cut Points |
|---|---|
| Elevated fasting glucose‡ (drug treatment of elevated glucose is an alternate indicator) | ≥100 mg/dL |

HDL-C = high-density lipoprotein cholesterol.
†The most commonly used drugs for elevated triglycerides and reduced HDL-C are fibrates and nicotinic acid. A patient taking 1 of these drugs can be presumed to have high triglycerides and low HDL-C. High-dose ω-3 fatty acids presumes high triglycerides.
‡Most patients with type 2 diabetes mellitus will have the metabolic syndrome by the proposed criteria.

"A therapeutically effective amount" means the amount of a compound that, when administered to a subject for treating a disease, is sufficient to effect such treatment for the disease. The "therapeutically effective amount" will vary depending on the compound, the disease and its severity and the age, weight, etc., of the subject to be treated.

Obesity affects one third of the adult population. Some have estimated the cost of obesity to be $117 billion per year. Generally, obesity has been viewed as the end result of eating too much and exercising too little, with the consequence that the excess energy is converted to fat. While the concept that obesity may represent a disease process has been considered, no specific mechanism has been discovered. As such, treatments focus on lifestyle modification, drugs aimed at decreasing food absorption or stimulating the sympathetic nervous system, or bariatric surgery. Despite best efforts, obesity continues to increase every year, and new approaches are needed.

Surprisingly and unexpectedly, the present inventors have discovered that the system of fat accumulation and fat utilization is tightly controlled and involves a molecular switch that is governed by the utilization of adenosine monophosphate (AMP). See FIGS. 1A and 1B. In particular, FIG. 1A shows that AMP is generated during RNA degradation, ATP depletion, and following fructose ingestion. In turn, AMP can engage AMP kinase resulting in the stimulation of fat oxidation and ATP generation. In contrast, if AMPD is active, and in particular AMPD2 is activated in the liver, then AMP is shunted to IMP and other purine degradation products such as uric acid. In humans, uric acid accumulates due to a mutation in uricase. The elevation in uric acid induces oxidative stress in the mitochondria, which, along with other products such as IMP, results in fat storage (resulting in obesity), fatty liver, diabetes, high blood pressure, and cardiovascular disease.

Figure 1B:
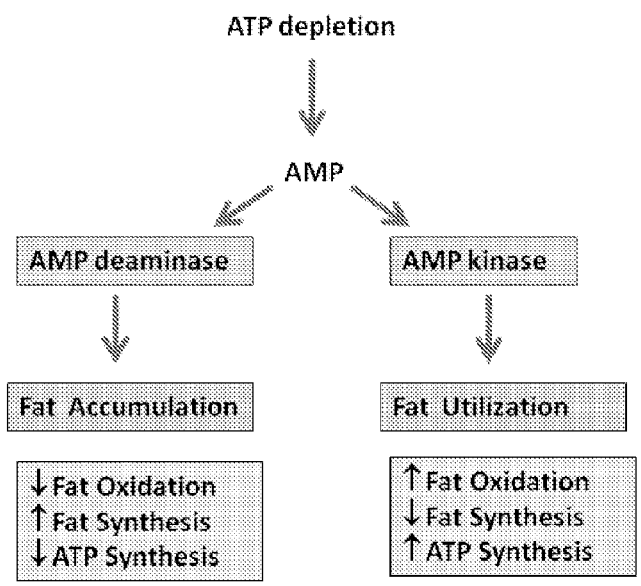

FIG. 1B shows that AMP that is generated from ATP depletion, can activate either AMP kinase or AMP deaminase. Whereas the activation of AMP kinase results in fat oxidation and a reduction in fat synthesis, the stimulation of AMP deaminase causes fat accumulation by blocking fat oxidation, stimulation of fat synthesis, inhibition of ATP synthesis, and the inhibition of AMP kinase. The present inventors have found that inter alia if sufficient AMP is available to activate AMP-activated protein kinase, then there is fat utilization, the blockade of fat synthesis, the stimulation of fat oxidation, and the production of ATP. In contrast, if AMP is shunted to uric acid via activation of AMP deaminase, then there is fat accumulation due to the stimulation of fat synthesis and the reduction in fat oxidation with a relative inhibition of ATP synthesis. Without being bound by any theory, it is believed that this effect is not simply due to a reduction in AMP kinase; rather, the shunting of AMP via the AMP deaminase pathway actively results in the accumulation of purine products that induce obesity via a specific mitochondrial mechanism that the present inventors have discovered. In particular, downstream products of the AMP deaminase pathway such as IMP and uric acid can induce mitochondrial dysfunction resulting in a relative depletion of adenosine triphosphate (ATP), the stimulation of fatty acid synthase, and the inhibition of enoyl CoA hydratase resulting in impaired fat oxidation.

The present inventors have also discovered that in some instances the switch from fat accumulating to fat utilizing requires both a reduction in AMP deaminase as well as a stimulation of AMP kinase, and that this is the mechanism by which the 13-line ground squirrel is able to hibernate. Specifically, AMPD2 is activated in the liver of squirrels as they try to increase their hepatic fat stores in preparation for hibernation, only to be turned down or off when they hibernate so they can then oxidize fat. In contrast, for humans AMP deaminase can become chronically activated and this may be largely responsible for the obesity epidemic. Specifically, AMPD2 is activated in the liver in response to fructose, and fructose intake is excessive in a large percent of the population due to ingestion of added sugars such as sucrose and high fructose corn syrup. In addition humans are more sensitive to the effects of fructose and have a greater AMPD2 response in part because of two mutations that humans carry. The uricase mutation results in higher uric acid levels and increases fructose effects by amplifying its metabolism by increasing expression of its transporter in the bowel and by increasing the activity of fructokinase leading to a greater depletion in ATP and a greater activation of AMPD2. The second mutation, of L gulono lactone oxidase that results in a loss of vitamin C synthesis which is a natural antioxidant that blocks the prooxidative effects of uric acid and fructose which is one way AMPD2 activation leads to fat accumulation.

AMP Deaminase (AMPD; EC. 3.5.4.6) is an enzyme that removes an amino functional group from AMP to generate inosine monophosphate (IMP). IMP is broken down by 5'-nucleotidase (EC 3.1.3.5) to inosine and then by purine nucleoside phosphorylase (PNP) to hypoxanthine, and then by xanthine oxidoreductase to xanthine and uric acid. AMP Deaminase includes a conserved C terminal with an ATP binding site with divergent N terminal domains that confer different specificities.

AMP Deaminase consists of 3 major isoforms identified to date, including AMPD1 (the M isoform) which exists as two subisoforms (from two mRNAs) due to alternative splicing. AMPD1 is expressed in skeletal muscle and to a lesser extent in heart. In contrast, AMPD2 (the L isoform) has 3 distinct mRNAs based on both different promoters as well alternative splicing. AMPD2 is the primary AMPD isoform present in the liver. See FIG. 2. Finally, AMPD3 (E isoform) is present in the heart and erythrocytes but also in other tissues and for which 4 mRNAs have been identified due to 3 different promoters and alternative splicing.

Some have suggested that AMPD1 may utilize AMP substrate and reduce the activation of AMP kinase as a mechanism for preventing metabolic syndrome and diabetes. For example, Goodarzi et al. (*Diabetes*, 2005, 54, 1222-7) reported that polymorphism of AMPD1 modulated insulin clearance in adults, suggesting a potential role for AMPD1 in diabetes. Safranow et al. (*Scand J Clin Lab Invest.*, 2009, 69, 102-12) reported that the C34T AMPD1 polymorphism which results in reduced AMPD1 activity was associated with features of the metabolic syndrome. These authors evaluated subjects with either congestive heart failure or coronary artery disease. In the subjects with coronary artery disease, the AMPD1 polymorphism was associated with lower body mass index, less obesity, lower waist circumference and less diabetes; for subjects with heart failure, the AMPD1 polymorphism was associated with lower fasting glucose levels and lower blood pressure. However, neither group showed a relationship of the polymorphism to serum triglycerides or cholesterol, or with renal function. Other studies have linked AMPD1 polymorphisms with improved outcomes in heart failure (see, for example, Loh et al., Circulation, 1999, 99, 1422-5; Gastmann et al., The American journal of cardiology, 2004, 93, 1260-4; and Yazaki et al., J Card Fail, 2004, 10, 316-20) and coronary artery disease (Anderson et al., J. Amer. College of Cardiology, 2000, 36, 1248-52).

While the Safranow et al. and Goodarzi et al. references suggest AMPD1 may be involved in diabetes and metabolic syndrome, other studies investigating AMPD 1 have not been able to repeat the finding. For example, three other studies could not find an association of body mass index with AMPD1 polymorphisms. See Kolek et al., J Card Fail, 2005, 11, 677-83; Collins et al., Am Heart J., 2006, 152, 312-20; and Agewall et al., Pathophysiol Haemost Thromb., 2006, 35, 440-4. Other studies also found no significant relationship of the AMPD1 polymorphism with weight. See Rico-Sanz et al., Physiol Genomics, 2003, 14, 161-6; Fischer et al., J Appl Physiol., 2007, 103, 315-22; and Hand et al., Life sciences, 2006, 79, 1413-8 Likewise, other studies could not find an association of AMPD1 with diabetes. See Yazaki et al., J Card Fail, 2004, 10, 316-20; Kolek et al., J Card Fail, 2005, 11, 677-83; Collins et al., Am Heart J., 2006, 152, 312-20; and Andreassi et al., Int J Cardiol., 2005, 101, 191-5. These inconsistent studies make uncertain whether blocking AMPD1 can be used to treat obesity or diabetes.

AMP deaminase inhibitors are known. For example, an early AMP deaminase inhibitor, Coformycin (carbocyclic coformycin), was originally developed as a herbicide. It was found that this compound also inhibits both AMP Deaminase and to a much greater extent, adenosine deaminase. Related compounds such as carbocyclic nebularine, deaminoformycin, and deoxycoformycin (pentostatin, see FIGS. 8B and 8C) also block both adenosine deaminase and AMP deaminase. Unfortunately, inhibition or deficiency of adenosine deaminase results in a severe immunosuppressed state with marked increase mortality. Therefore, in order to be therapeutically useful a compound needs to selectively inhibit AMP Deaminase, in particular AMPD2, but does not significantly modulate adenosine deaminase.

Some AMP Deaminase inhibitors that are selective for AMPD and do not significantly inhibit adenosine deaminase are known. For example, Kasibhatla (see J Med Chem., 2001, 44, 613-8) developed inhibitors generated by the substitution of aliphatic and alkylaryl groups with carboxylic acids at the N3 position of the aglycon of coformycin that has shown to selectively inhibit AMP deaminase with Ki as low as 0.002 µM and which have minimal activity for adenosine deaminase (see compound 24b, 3-[2-(3-carboxy-4-bromo-5,6,7,8-tetrahydronaphthyl)ethyl]-3,6,7,8-tetrahydroimidazo[4,5-d][1,3]diazepin-8-ol). This inhibitor was found to inhibit purified human cardiac AMP deaminase at 0.5 µM and the enzyme in isolated cardiomyoctes at a concentration of 0.5 mM without a significant toxicity. Unfortunately, these agents are nonspecific AMPD inhibitors and are not specific for any of the AMPD isoforms.

U.S. Pat. Nos. 4,912,092 and 5,731,432 discuss various AMP deaminase inhibitors to treat or prevent a variety of cardiovascular and other disorders. However, these patents do not mention treating diabetes, obesity or kidney disease. More significantly, these patents do not show any evidence that these agents are isoform specific nor do they discuss the importance of blocking AMPD2. These patents state that the disclosed compounds work by increasing adenosine and hence blood flow. Unfortunately, while adenosine may improve vascular conditions by increasing blood flow, recent evidence suggests adenosine may increase the risk for obesity and fatty liver, not the converse. Importantly, these patents do not teach the use of AMPD2 specific inhibition in the treatment of fatty liver, obesity, diabetes, metabolic syndrome or kidney disease.

Fructose is known to increase AMP deaminase activity in the liver. The primary isoform of AMPD in the liver is AMPD2. Unlike AMPD1, it has been shown that binding of ATP increases AMPD2's affinity for substrate. In addition, AMPD2 has marked differences from AMPD 1 at the N-terminal region. The present inventors have discovered the role for AMPD2 activity in the liver that induces fatty liver and obesity. The present inventors have shown this by examining the effects of fructose in inducing fatty liver and metabolic syndrome in both in vitro and in vivo models and also by examining the direct effects of downstream products of AMPD (e.g. uric acid) on both hepatic and other cell types and also in in vivo models.

The present inventors have identified one of the key roles for AMPD, and specifically isoform AMPD2, in driving obesity, fatty liver, insulin resistance, diabetes, kidney disease, and other clinical conditions associated with the metabolic syndrome. The expression of AMPD2 in the liver, kidney and pancreas is associated with toxicity at these sites when it is engaged. Engagement can occur by excessive intake of fructose, or by mechanisms that lead to a rise in uric acid as uric acid regulates fructose metabolism and hence acts as a positive feedback. Accordingly, some aspects of the invention provide methods for treating a clinical condition associated with the metabolic syndrome by inhibiting AMPD (typically the AMPD2 isoform), stimulating AMP activated protein kinase (using, for example, metformin), or a combination thereof. It should be appreciated that a combination of inhibitors that act on other isoforms can also be used. Since AMPD1 is believed to regulate insulin uptake in skeletal muscle, in some instances a combination of AMPD2 and AMPD 1 inhibitors can be beneficial to prevent the development of diabetes. In other embodiments, methods of the invention include inhibiting AMPD2 and AMPD3. AMPD inhibition that effectively reduces AMPD2 and with modest reduction in AMPD 1 and/or AMPD3 can also be used to prevent obesity and diabetes. Combination of AMPD inhibitors (including AMPD2 inhibitors) with allopurinol or other xanthine oxidase inhibitors can also be used. In addition, a combination of agents that block uric acid uptake into hepatocytes or vascular cells (such as probenecid and other inhibitors of URAT1) can also be used in addition to an AMPD2 inhibitor.

Some aspects of the invention are based on the discovery by the present inventors of the importance of AMPD, especially AMPD2, in driving obesity, fatty liver, kidney disease, pancreatic injury, diabetes, and other clinical conditions associated with metabolic syndrome. The present inventors have discovered that activation of AMPD not only shunts AMP away from AMP activated protein kinase but also generates products such as IMP and uric acid that have direct effects to reduce ATP levels, stimulate fat synthesis, and block fat oxidation. This activity has downstream effects on insulin resistance, diabetes, hypertension, microvascular disease, systemic inflammation, endothelial function, oxidative stress, plasma triglycerides, HDL cholesterol, uric acid levels, weight control, as well as other clinical conditions associated with metabolic syndrome.

Unlike conventional AMPD inhibitors, some embodiments of the invention are directed to treating clinical conditions associated with metabolic syndrome and other metabolic diseases. In some instances, methods of the invention are directed to modulating, often inhibiting, AMPD2 with or without inhibition of the other AMPD isoforms. It should be appreciated that an AMPD2 inhibitor can be used in combination with other drugs to potentiate its effects. This can include a wide variety of agents, including uric acid lowering drugs, AMP kinase stimulants, other agents used to treat diabetes including thioglitazones, antioxidants including ascorbate and resveratrol, and the catechins and flavenoids present in tea, cocoa and other nutrients.

Figure 17:
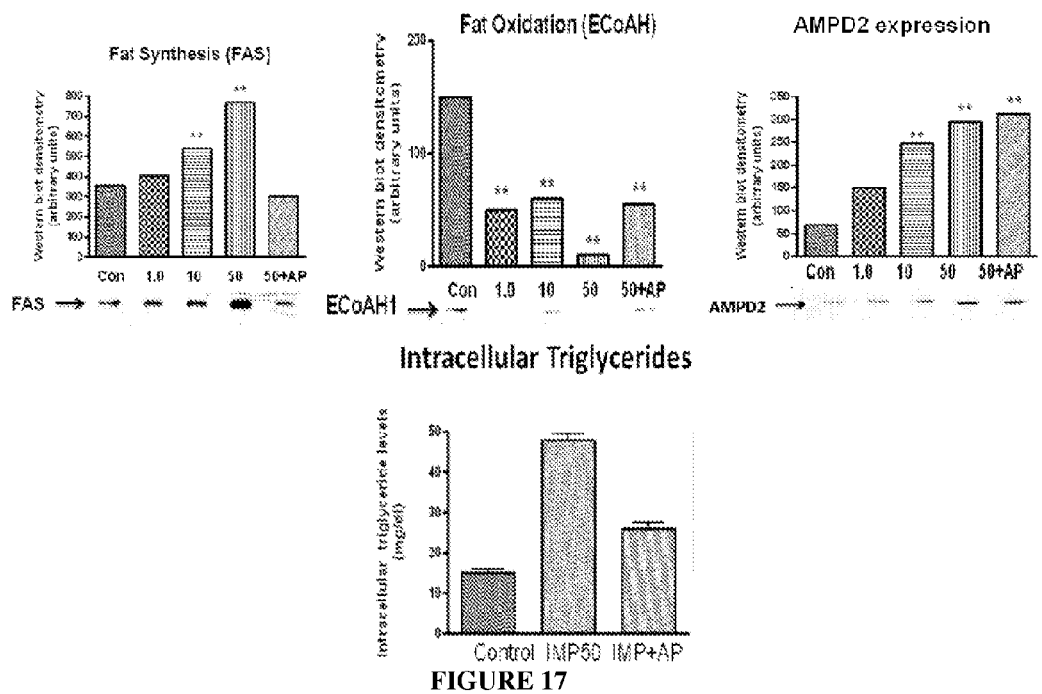

Methods of the invention are superior to simple reduction of uric acid with xanthine oxidase inhibition or other uric acid lowering drugs. For example, there is increasing evidence that purines acting prior to xanthine can also contribute to fat accumulation (see FIG. 17 for effect of IMP on enoyl CoA hydratase and triglycerides). This includes studies showing increased fat accumulation in kidneys of xanthine oxidase knockout mice, studies showing that adenosine may have a role in fatty liver induced by alcohol, and studies such as shown in FIG. 17 showing that allopurinol (which lowers uric acid) cannot block all of IMP associated effects.

In some embodiments, relative to the selectivity of other AMPD isoforms, methods of the invention include using a compound that is selective for AMPD2 inhibition for treating a clinical condition associated with the metabolic syndrome. In some instances, a compound that is at least 2×, typically 10×, more typically 50×, often 100×, more often 200×, still more often 500× and most often 1000× selective for AMPD2 relative to other isoforms of AMPD and/or adenosine deaminase is used in methods of the invention. Yet in other embodiments, the compound's selectivity for AMPD2 inhibition is 10× or above, and typically 100-1000×.

Methods of the invention can be used to treat (e.g., prevent, ameliorate, or reduce) obesity, diabetes, fatty liver (both non-alcoholic and alcoholic fatty liver diseases), chronic kidney disease, diabetic nephropathy, pulmonary hypertension, systemic hypertension, and systemic inflammation such as C reactive protein levels. Exemplary fatty liver include nonalcoholic hepatic steatosis, alcoholic hepatic steatosis, and steatosis associated cirrhosis.

Methods of the invention can also be used to reduce plasma triglycerides, to preserve pancreatic islet function, to improve oxidative stress (such as by reducing urinary isoprostanes), to improve vascular function (such as improving brachial artery reactivity), to raise HDL cholesterol, and to reverse microvascular disease.

Methods of the invention can be used in combination with other drugs such as recombinant or pegylated uricase, Puricase, KHK inhibitors, metformin, thiazolidinediones, ACE inhibitors, Angiotensin receptor blockers, aldose reductase inhibitors, thiazide diuretics, antioxidants such as vitamin C, catechins, resveratrol, and uric acid lowering drugs (e.g., xanthine oxidase inhibitors or uricosuric agents). Such drugs are well known to one skilled in the art can the list of such drugs can be readily found, for example, in Merck Index.

Methods of the invention can be practiced by using a selective AMPD2 inhibitor, an AMPD2 antibody, an AMP analog that inhibit AMPD2, a siRNA that block expression of AMPD2, paninhibitors of AMPDX that inhibit AMPD2, a carbocyclic coformycin or its derivative, a carbocyclic nebularine or its derivative a deaminoformycin or its derivative, or any of the compounds disclosed in U.S. Pat. Nos. 4,912,092 and 5,731,432.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

Expression of AMPD2 in Liver Cells

Figure 2:
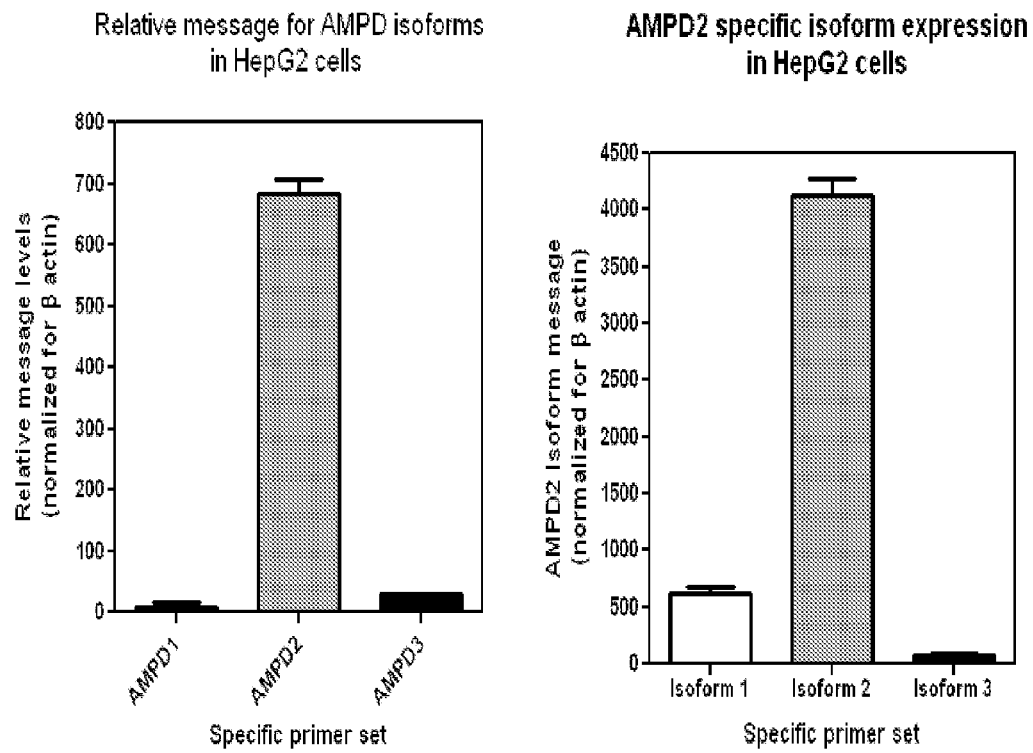
FIG. 2 is a graph showing the relative amounts of differenet isoforms of AMPD in liver cells.

AMPD2 is specifically expressed by hepatic cells and is primarily of the isoform 2 type of AMPD2 (FIG. 2).

Example 2

Studies With Antisense to AMPD2 mRNA

Figure 3:
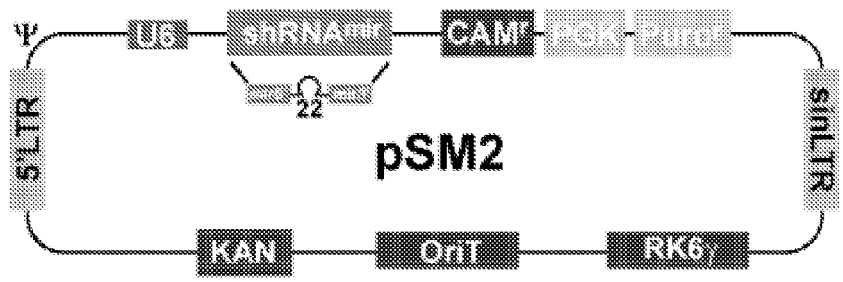
FIG. 3 is a schematic representation of a vector that is used to silence AMPD2. A plasmid-based siRNA vector system is employed expressing RNAs under the U6 promoter in transfected mammalian cells. RNAs are expressed as fold-back stem-loop structures that are processed into the siRNAs.

An shRNA for AMPD2 was employed to silence human hepatic cells (HepG2). (FIGS. 3 and 4) The silencing vector pSM2-AMPD2 (V2HS_172668, Open Biosystems) incorporates a 22-base shRNAmir trigger designed to mimic a natural microRNA primary transcript. The target sequence is specific for human AMPD2 and has been selected based on thermodynamic criteria for optimal small RNA performance. The specific sequence is 5'-ACCTGGGAATCTGCTCAT-TGTT-3'(SEQ ID NO: 1).

Figure 4:
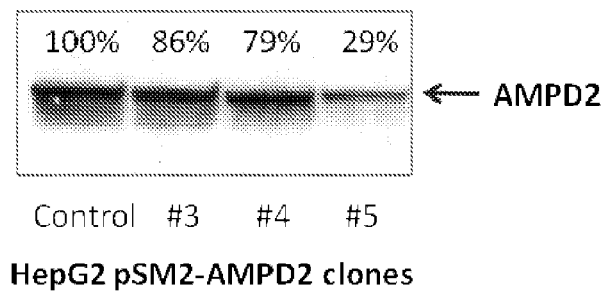
FIG. 4 shows Western blot of control and cells that were AMPD2 silenced using the AMPD2 silencing vector (sAMPD2).

The immortalized human hepatocytes cell line, HepG2, was transfected with the silencing vector pSM2-AMPD2 using Lipofectamine LTX Plus (Invitrogen) as described by the manufacturer (FIG. 4). Briefly, cell cultures were grown to 90-95% confluence in normal growth media and in 24-well plates. Lipid-DNA complexes were prepared as per recommended protocols using growth media without serum. 100 µl of the lipid-DNA solution was added per well of attached cells and incubated for 4 hrs at 37° C. Wells were then diluted with 1.5 ml of normal growth media and incubated for an additional 24 hrs prior to addition of selective media containing 1 µg/mL Puromycin antibiotic. After 7 days, stable transfectants (clones) were selected with glass cloning rings, replated and a second colony selection was performed to provide a clean clone for analysis. Validation of AMPD2 gene knock down was performed by harvesting protein and performing a Western blot for protein expression. Clone #5 was subsequently used for the experiments and was designated as sAMPD2.

Figure 5A:
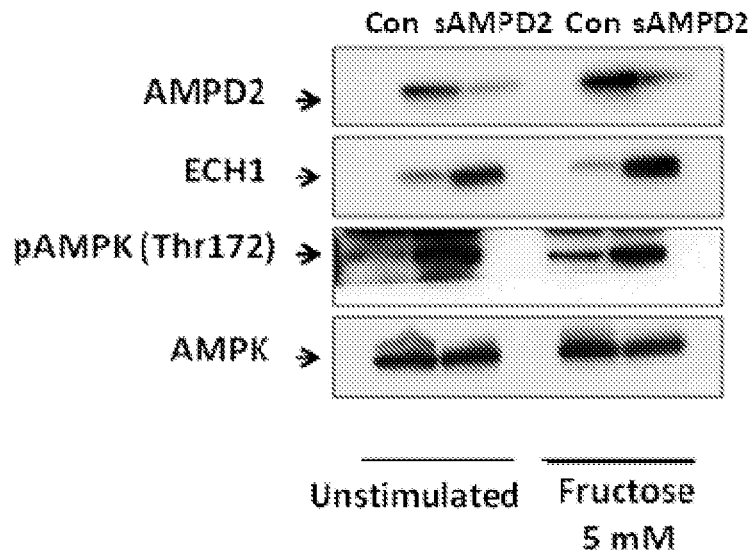
FIGS. 5A and 5B are a Western blot and a graph, respectively, showing that β-fatty acid oxidation, as measured by β-hydroxybutyrate, increased with silencing of AMPD2 in HepG2 cells in both unstimulated hepatocytes and hepatocytes stimulated with fructose.

As shown in FIG. 5A, control (Con) human HepG2 cells express AMPD2 which was reduced in the presence by knockdown with shRNA to AMPD2. Fructose treated hepatocytes express increased AMPD2 but this was also blocked by shRNA (sAMPD2). A key enzyme in Beta fatty acid oxidation, enoyl CoA hydratase-1 (ECH-1), was stimulated in control cells as well as fructose treated cells in which AMPD2 had been silenced. The inhibition of AMPD2 by sAMPD2 was accompanied by an upregulation of phosphorylated AMPkinase (Thr172) in both unstimulated and fructose stimulated hepatocytes, whereas total AMPK was not altered.

Figure 5B:
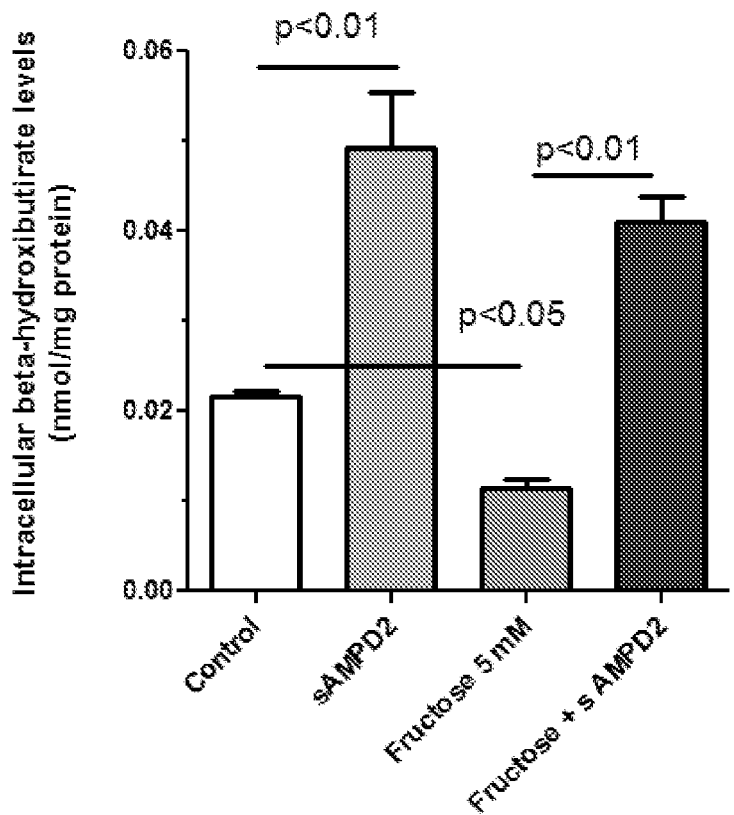

The stimulation of fat oxidation in AMPD2 knocked down hepatocytes was confirmed by measuring β hydroxybutyrate, a fat oxidation product (FIG. 5B). FIG. 5B shows that beta fatty acid oxidation, as measured by beta hydroxybutyrate, increased with silencing of AMPD2 in these same cells in both fructose-stimulated and unstimulated cells. This indicates that blocking AMPD2 will stimulate fat oxidation. This result also suggests that this is a great target for obesity.

Figure 6A:
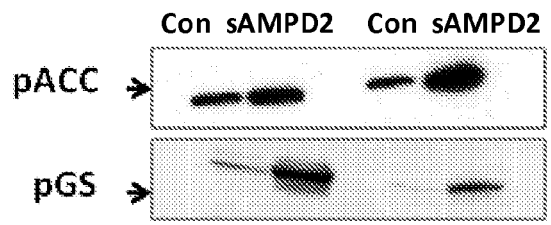
FIGS. 6A and 6B are a Western blot and a graph, respectively, showing that knockdown of hepatic AMPD2 activity results in the phosphorylation of target genes involved in both triglyceride synthesis (phosphorylated acetyl CoA carboxylase, pACC) and glycogen synthesis (phosphorylated glycogen synthase, pGS) with an increase in intracellular triglycerides.
Figure 6B:
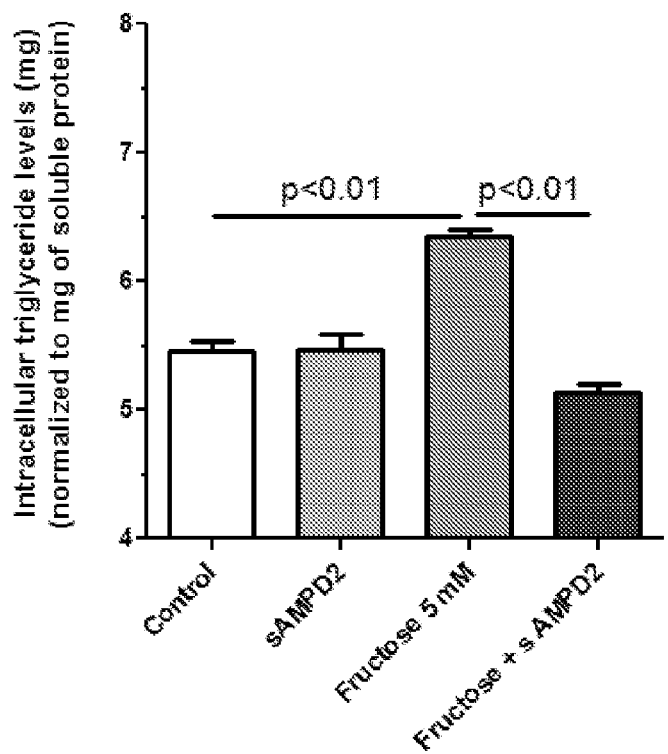

The stimulation of phosphorylated AMP kinase in human hepatocytes (HepG2 cells) by silencing AMPD2 with shRNA as shown in FIG. 5A led to inhibition of target genes as noted by Western blot (FIG. 6A). For example, the phosphorylated form of Acetyl CoA Carboxylase (pACC) which is involved in triglyceride synthesis was induced by silencing AMPD2 in both unstimulated and fructose stimulated cells. Likewise, the phosphorylated form of glycogen synthase (pGS) was also induced in AMPD2 silenced HepG2 cells both under unstimulated conditions and in the presence of fructose. Importantly, these changes blocked the triglyceride accumulation in HepG2 cells in response to fructose (FIG. 6B). FIG. 5 shows that knocking down AMPD2 in cells resulted in blocking the triglyceride (fat) accumulation in cultured hepatocytes (HepG2) cells in response to fructose.

Figure 7A:
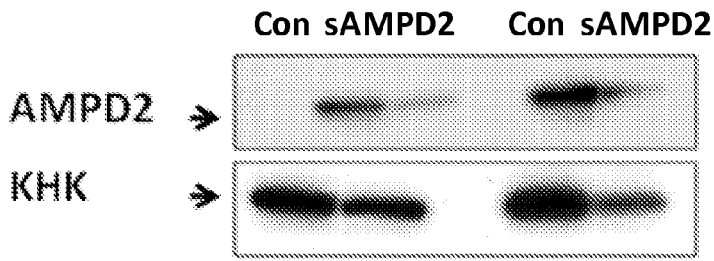
FIGS. 7A and 7B are a Western blot and a graph, respectively, showing that knockdown of hepatic AMPD2 activity reduces the expression of fructokinase (KHK) and minimizes the reduction of intracellular free phosphate in response to fructose
Figure 7B:
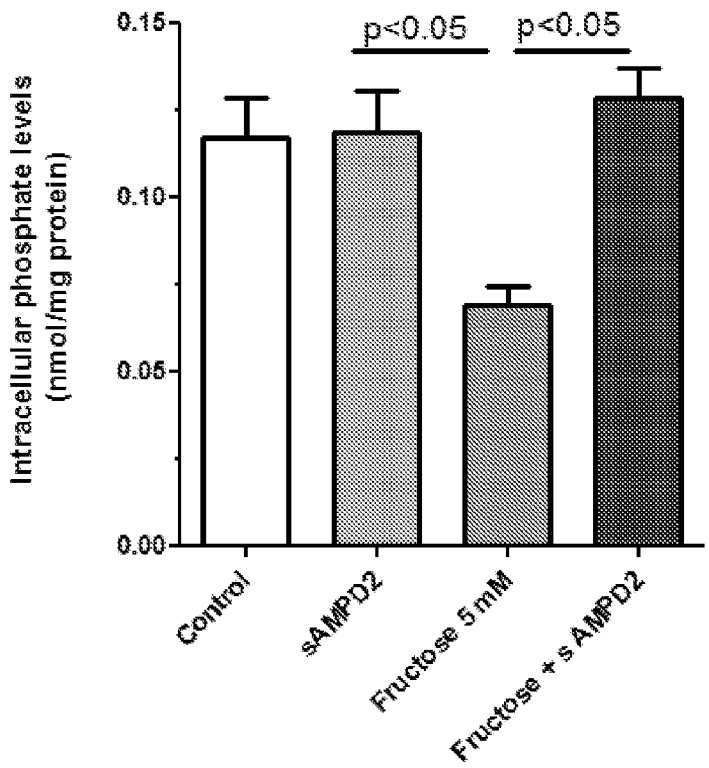

Fructokinase (KHK), the primary enzyme involved in fructose metabolism, is upregulated by fructose, and likewise the present inventors have found that 5 mM fructose can stimulate KHK in HepG2 cells (FIG. 7A). Silencing AMPD2 prevented the upregulation of KHK in response to fructose. Furthermore, the phosphorylation of fructose by KHK resulted in an acute decrease in intracellular phosphate which is a known stimulant of AMPD2 activity. However, AMPD2 silenced cells showed less phosphate depletion with fructose (FIG. 7B), consistent with the discovery that the upregulation of KHK by fructose was blocked by AMPD2 silencing. Hence, some of the benefit of silencing AMPD2 may be by blocking the upregulation of fructokinase in response to fructose.

Example 3

Inhibitors of AMPD2

AMP deaminase activity was determined by estimating the production of ammonia by a modification of the method described by Chaney and Marbach. See, Chaney et al., *Clin Chem.*, 1962, 8, 130-132; Ito et al., *J Biochem.*, 1988, 103, 259-262; and Sims et al., *Neurobiol Aging.*, 1998, 19, 385-391. Briefly, the reaction mixture consisted of 25 mM sodium citrate, pH 6.0, 50 mM potassium chloride, and different concentration of AMP. The enzyme reaction was initiated by the addition of the enzyme solution and incubated at 37° C. for 15 min. The reaction was stopped with the addition of the phenol/hypochlorite reagents: Reagent A (100 mM phenol and 0.050 g/L sodium nitroprusside in $H_2O$) was added, followed by reagent B (125 mM sodium hydroxide, 200 mM dibasic sodium phosphate, and 0.1% sodium hypochlorite in $H_2O$) and incubated for 30 min at 25° C. The absorbance of the samples was measured at 625 nm with a spectrophotometer. To determine the absolute specific activity of ammonia production (micromoles ammonia/min), a calibration curve was determined in the range of 5 μM to 1 mM of ammonia.

Figure 8A:
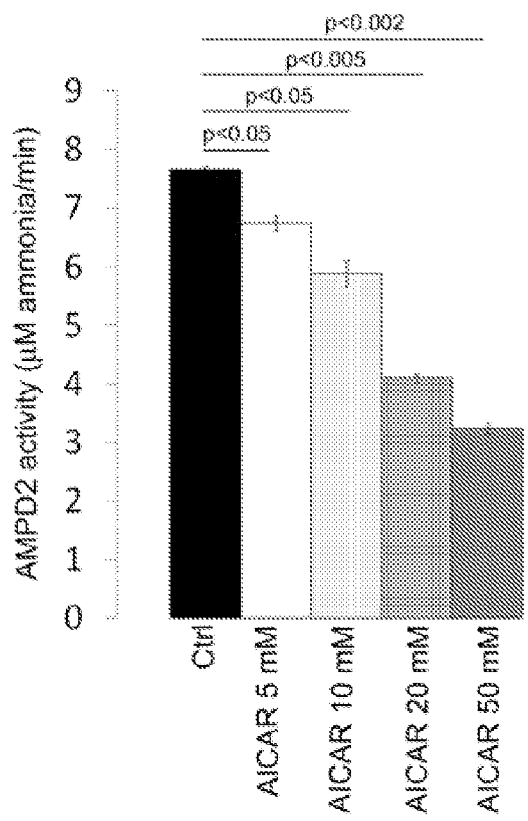
FIGS. 8A-8C are graphs showing that hepatic AMPD2 activity in response to AMP is blocked by AICAR and Deoxycoformycin (pentostatin)
Figures 8B, 8C:
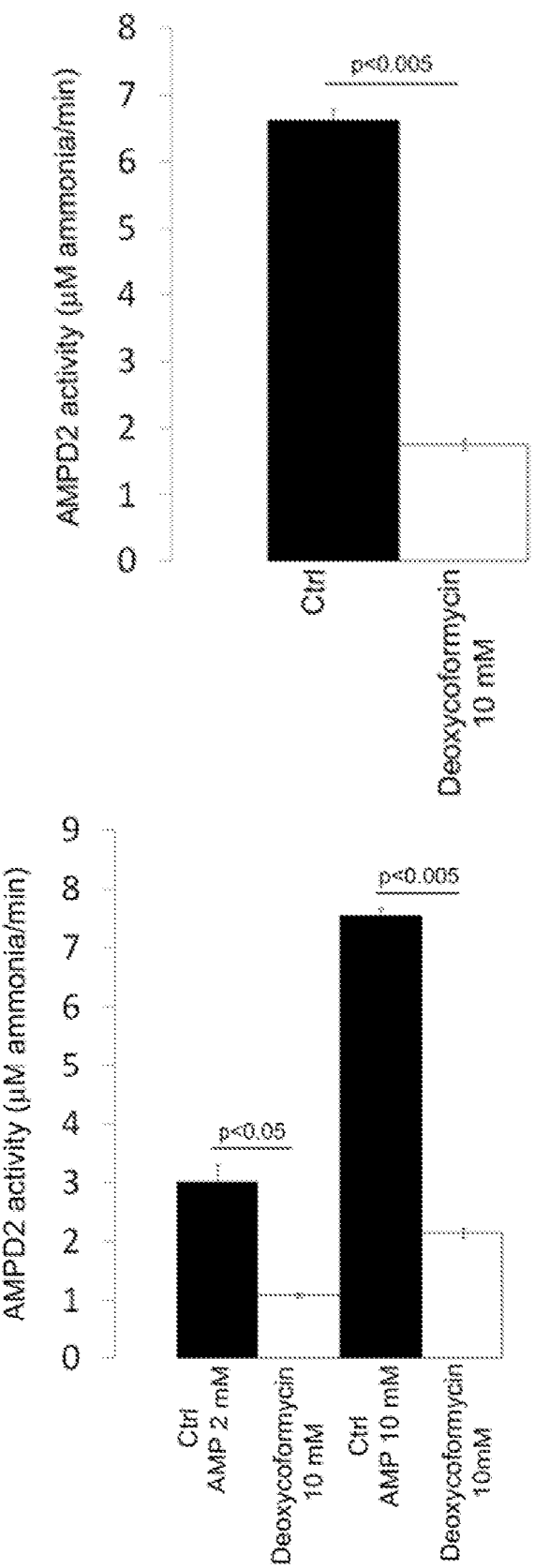

Using the procedure above, various AMPD2 inhibitors were assayed. As can be seen, aminoimidazole carboxamide ribonucleotide (AICAR) is an AMPD2 inhibitor (FIG. 8A). Likewise, deoxycoformycin (pentostatin) is also an AMPD2 inhibitor (FIGS. 8B and C). For this assay AMPD isolated from squirrel liver was used, which only expresses AMPD2 and not the other AMPD isoforms. As shown in FIGS. 8A-8C, it was found that AICAR inhibits AMPD2 activity in a dose dependent manner, in addition, deoxycoformycin markedly inhibits AMPD2 activity (64% and 72% in the presence of 2 mM and 10 mM AMP respectively).

Figure 9A:
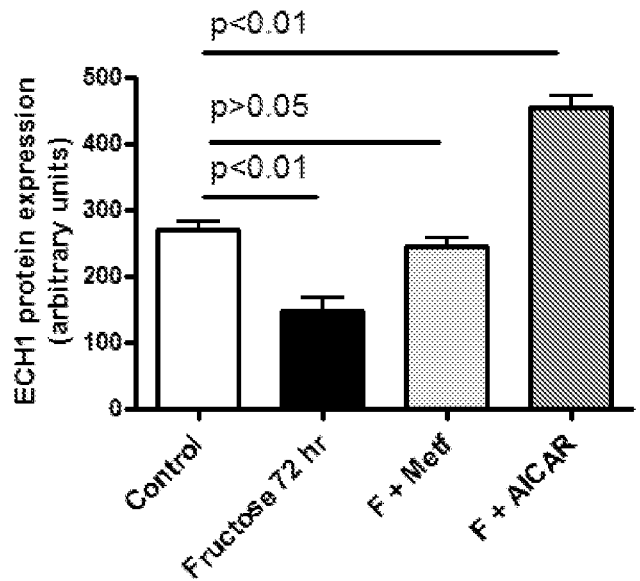
FIGS. 9A and 9B are graphs showing AICAR and Metformin stimulate fat oxidation and block triglyceride accumulation in response to fructose
Figure 9B:
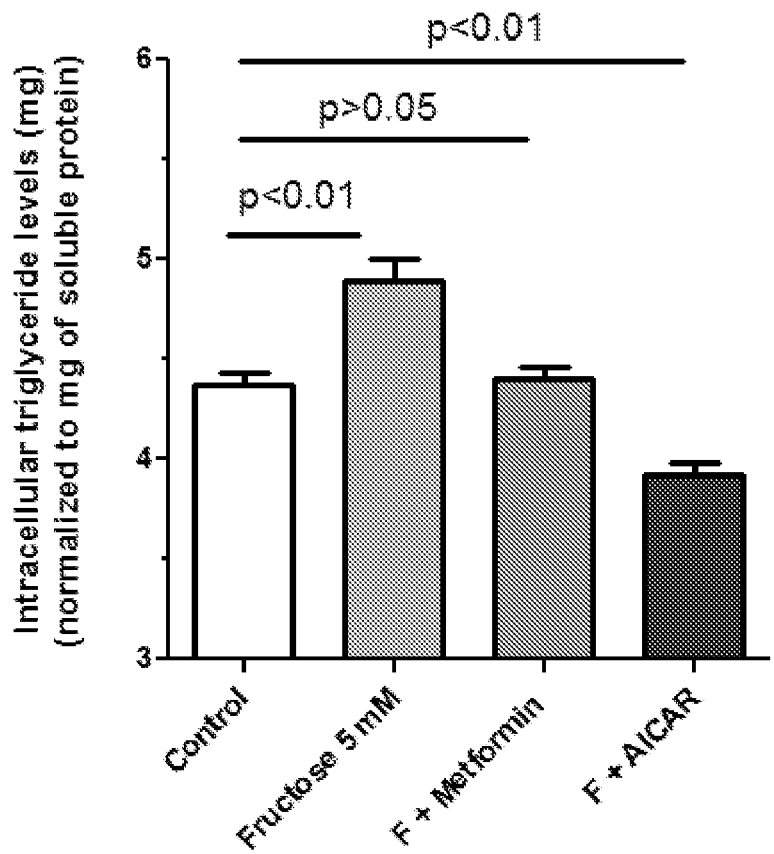

The stimulation of HepG2 cells with fructose (5 mM) for 72 hrs resulted in a fall in enoyl CoA hydratase-1 (ECH-1) levels as determined by densitometry of western blot samples, and this defect in fat oxidation was reversed by either metformin or AICAR. See FIGS. 9A and 9B. Consistent with an improvement in fat oxidation, both AICAR and metformin prevented the rise in intracellular triglycerides in response to fructose.

Example 4

Overexpression of AMPD2

Figure 10A:
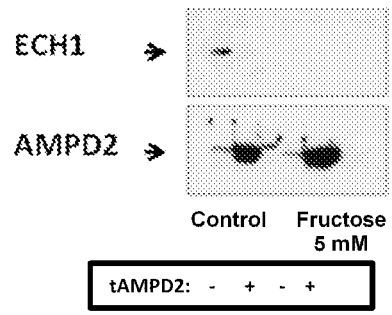
FIGS. 10A-10C are graphs showing overexpression of AMPD2 in HepG2 cells increased the lipogenic effects of fructose, resulting in enhanced intracellular triglyceride accumulation and reduced fat oxidation.
Figure 10B:
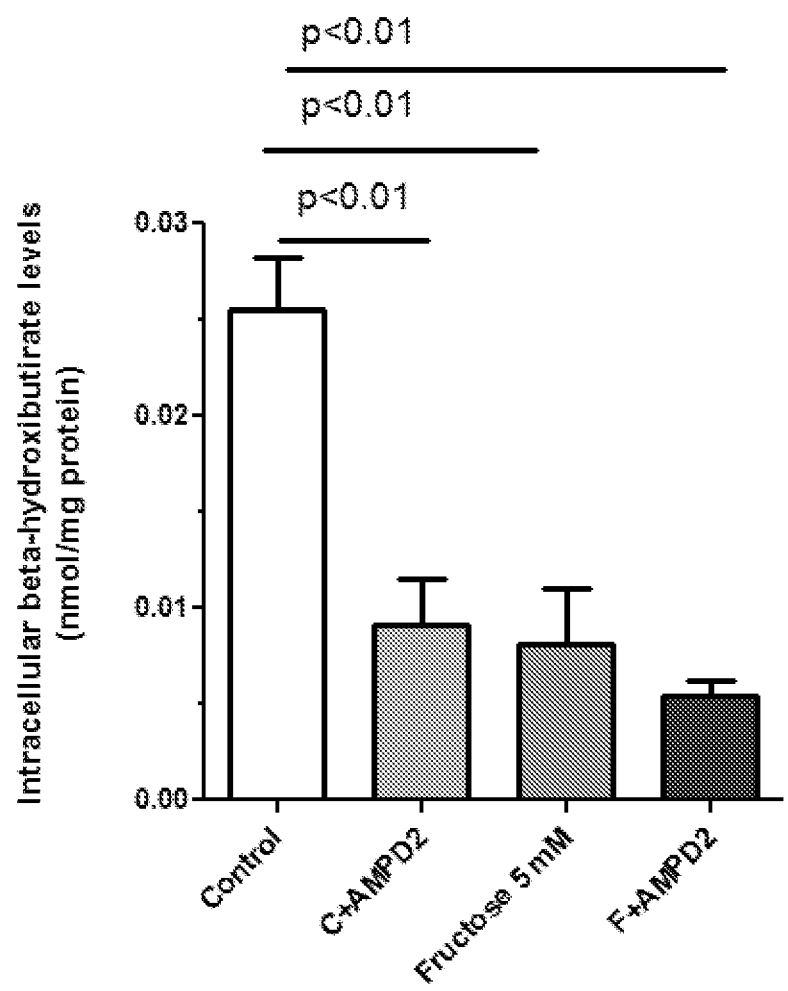
Figure 10C:
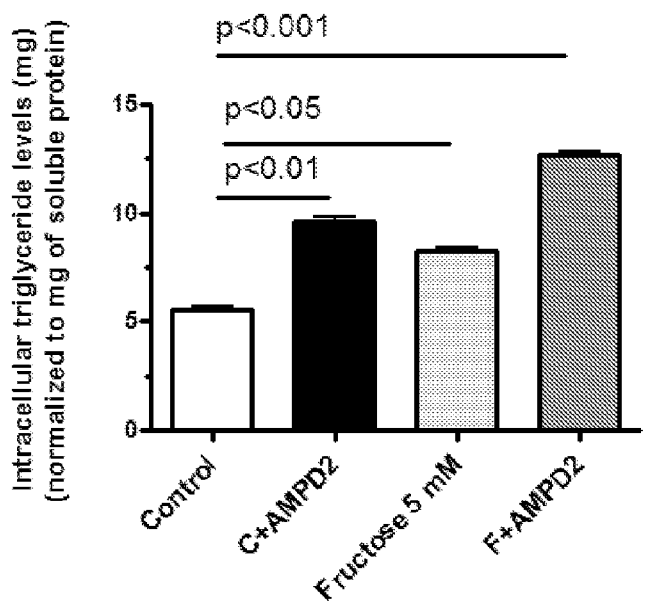

AMPD2 was overexpressed in transduced HepG2 cells with the lentiviral vector pLVX containing the isoform 2 of AMPD2. Clones overexpressing AMPD2 were selected with puromycin (2 μg/ml). As shown in FIG. 10A, the overexpression of AMPD2 (tAMPD2) was associated with a spontaneous reduction in expression of enoyl CoA hydratase-1 (ECH1) which is involved in fatty acid oxidation. Overexpression of AMPD2 also resulted in an inhibition of intracellular beta hydroxybutyrate accumulation (reflecting the block in fat oxidation) as well as an accumulation of triglycerides. These effects were compounded in cells treated with fructose (5 mM). FIGS. 10B-10C Example 5

Effects of Sucrose in the Livers of Rats

Figure 11A:
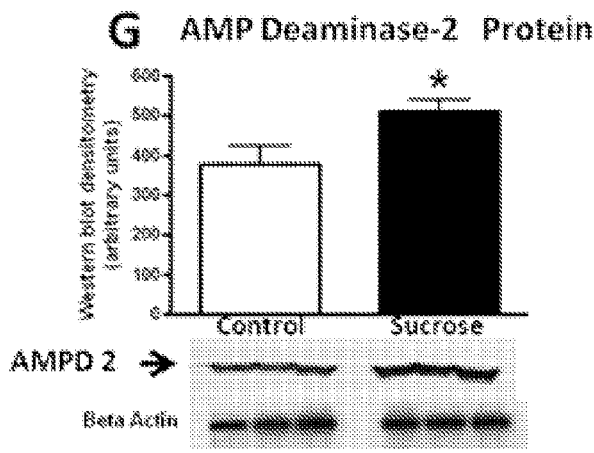
FIGS. 11A-11C are graphs showing that sucrose diet increases AMPD2 expression in the liver of rats.
Figure 11B:
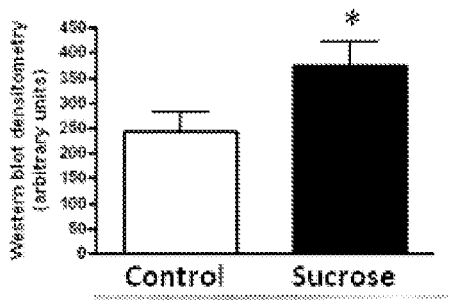
Figure 11C:
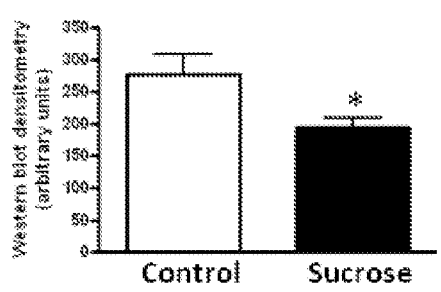

The administration of a 40% sucrose diet (which contains fructose) to rats for 4 months resulted in the development of metabolic syndrome and fatty liver; this was not observed in rats in which the sucrose diet was replaced by starch (control). FIGS. 11A-11C. Liver samples from the sucrose fed rats showed a marked increased level by western blot (shown by densitometry) for AMPD2 protein compared to control (starch-fed) rats. Likewise, this was associated with an increased fat synthesis (noted by an increase in FAS protein) and a decrease in fatty acid oxidation (noted by a reduction in enoyl CoA hydratase).

Example 6

Effects of AMPD Inhibition on Fructose Induced Fatty Liver

Figure 12A:
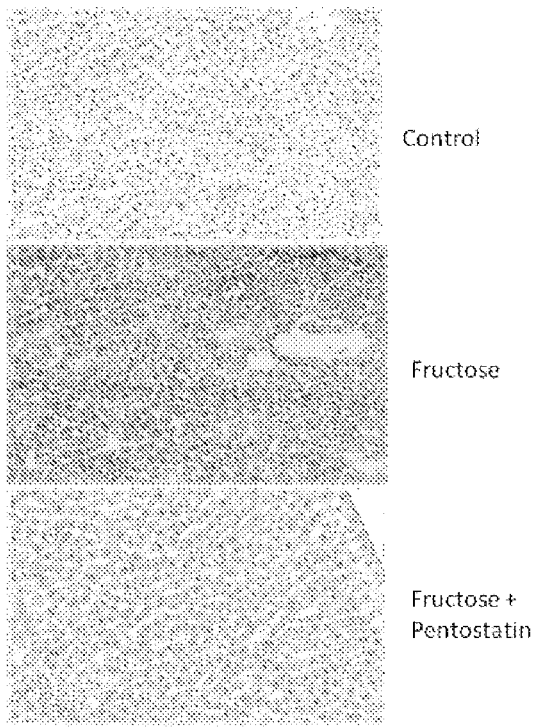
FIGS. 12A and 12B are slides and a graph, respectively, showing that pentostatin (deoxycoformycin) prevents fructose induced fatty liver in rats.
Figure 12B:
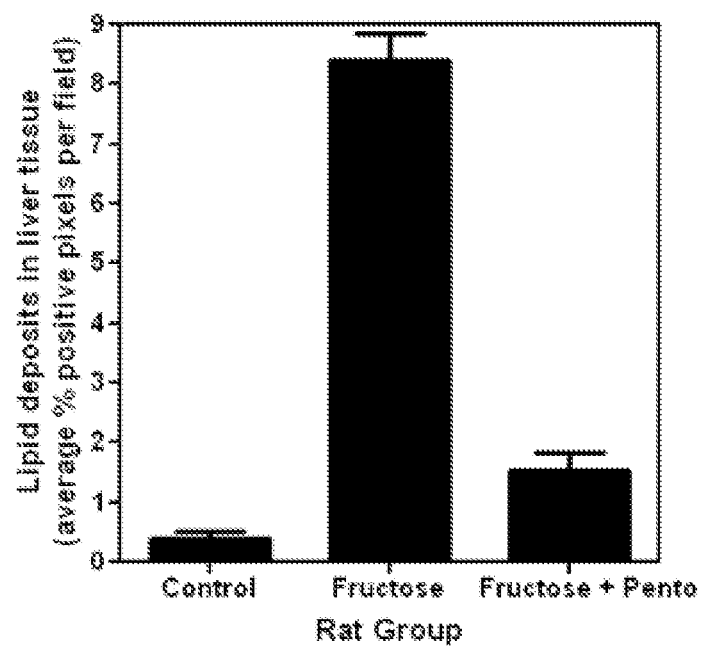

Male Sprague Dawley rats (350-400 g) were given fructose 20% in the water for two weeks with (n=12) or without (n=12) pentostatin 0.1 mg/kg daily i.p. A third set of rats received control diet (n=12). Fructose only and control diet rats also received daily i.p injections of vehicle. At the end of two weeks rats were sacrificed. Liver tissue from fructose fed rats showed marked fatty liver as determined by Oil Red O stain of cryostat fixed tissues. FIG. 12A. This was largely prevented by pentostatin, as determined by analysis of lipid deposits (average of 12 fields per biopsy) using positive pixil count softward (Aperio). FIG. 12B.

Figure 13A:
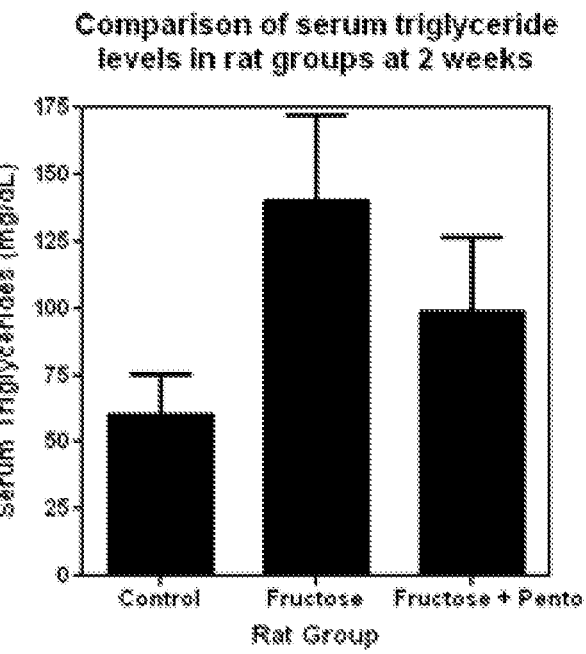
FIGS. 13A and 13B are graphs showing that pentostatin (deoxycoformycin) prevents fructose induced hypertriglyceridemia.
Figure 13B:
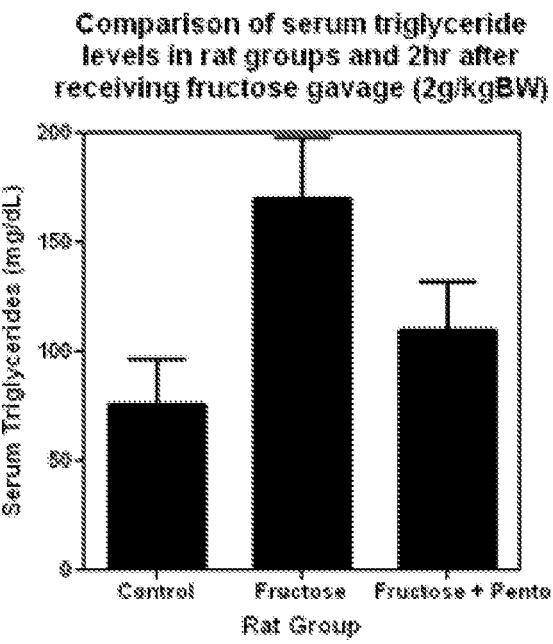

Pentostatin, which can function as an AMPD2 inhibitor, also significantly reduced the rise in fasting serum triglycerides in response to fructose at two weeks (FIG. 13A), but also blocked the rise in serum triglycerides at two weeks in response to a bolus of fructose (2 g/kg body weight) administered by gavage (FIG. 13B).

Example 7

Studies of AMPD2 in Hibernating Mammals

Figure 14A:
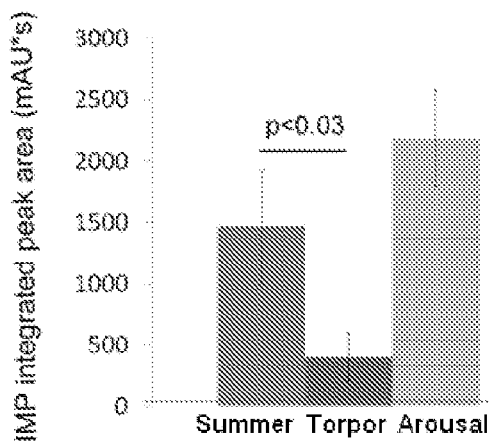
FIGS. 14A and 14B are graphs showing that AMP Deaminase was inhibited during torpor with activation of fatty acid oxidation and AMP kinase.

Hibernating mammals switch from fat accumulation to fat utilization via an AMPD2 dependent pathway. Just prior to hibernation, the 13 line ground squirrel develops obesity, fatty liver, insulin resistance, and hypertriglyceridemia in association with an elevation in serum uric acid. See Martin, *Diab Vasc Dis Res.*, 2008, 5, 76-81. As hibernation occurs, there is a significant fall in uric acid as well as its precursors xanthine and hypoxanthine, consistent with a significant inhibition of an enzyme proximal to xanthine, AMP deaminase. Consistent with these observations, we found that AMMPD2 activity, measured by the IMP content in liver samples by HPLC, fell as animals entered torpor only to rise again during interbout arousals (reflecting intermittent periods of warming) (FIG. 14A). AMPD2 enzyme reaction was initiated by the addition of homogenized liver and incubated with 12.5 mM AMP at 37° C. The reaction was terminated by addition of 4.5% perchloric acid. Acid extracts were neutralized and IMP produced was quantified by HPLC. The column was a ZORBAX Eclipse XDB-C18 with a mean particular size of 5 µm (Agilent).

Figure 14B:
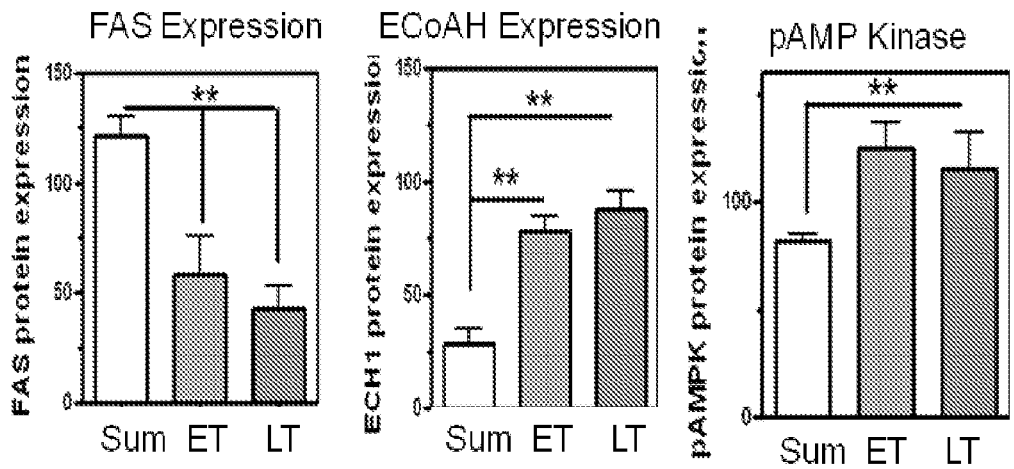

Shown in FIG. 14B are densitometry of western blots of liver tissue from these squirrels. The left panel of FIG. 14B shows that summer was associated with increased fatty acid synthase (FAS) expression, which falls with early and late torpor (ET and LT). In contrast, both fatty acid oxidation (Enoyl CoA hydratase) and phosphorylated AMP kinase were activated during torpor. These studies are consistent with the changes in AMPD2 activity shown in FIG. 14A.

Example 8

AMPD2 Regulation by Fructose

Figure 15:
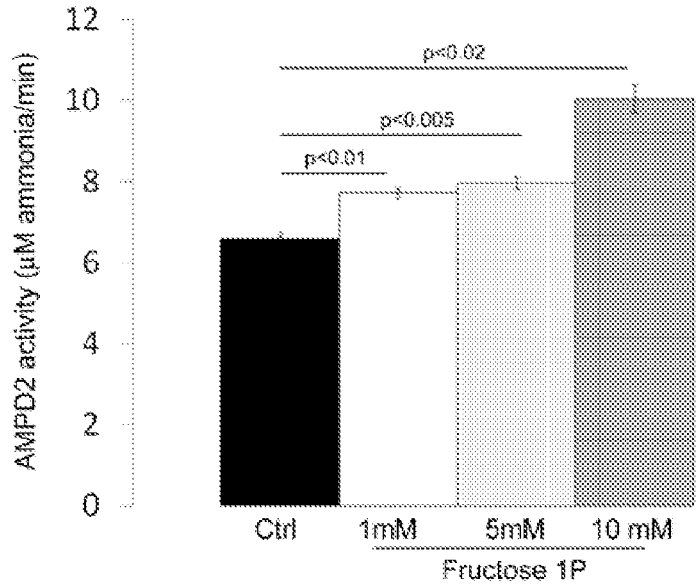
FIG. 15 is a graph showing that fructose-1-phosphate activates AMPD2

Fructokinase uses ATP to phosphorylate fructose to fructose-1-phosphate leading to a reduction of ATP and generation of AMP, leading to the activation of AMPD2. FIG. 15 shows that fructose-1-phosphate increases AMPD2 activity showing a direct relationship of AMPD2 with fructose metabolism.

Figure 16:
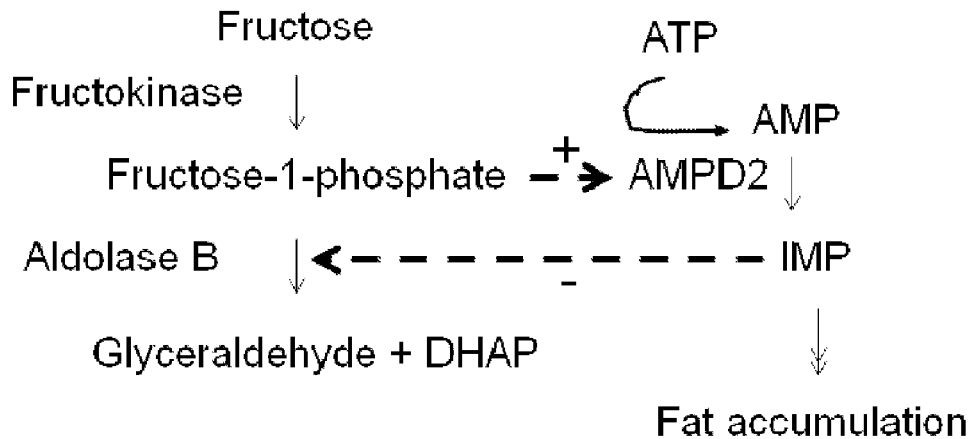
FIG. 16 is a schematic illustrating the activation of AMPD2 by fructose-1-phosphate thus activating the cycle induced by inhibition of aldolase by the AMPD2 product IMP FIG. 17 are Western blots showing that IMP (1-50 μM), the product of AMP metabolism by AMPD2 is able to up-regulate fatty acid synthase (FAS) and AMPD2 expression with parallel down-regulation of the fat oxidation as noted by Enoyl-CoA Hydratase (ECoAH). Allopurinol (AP) cannot fully rescue the reduction in ECoAH is consistent with IMP having direct effects to inhibit fat oxidation. IMP also stimulates triglyceride accumulation and is blocked by allopurinol. These studies show that the AMPD2 product, IMP, can stimulate fat accumulation by both stimulating fat synthesis and blocking fatty acid oxidation.

FIG. 16 shows a schematic of the interrelationship of AMPD2 regulation during the metabolism of fructose. During fructose metabolism AMPD2 is stimulated by fructose-1-phosphate in a positive feedback loop; likewise, IMP, the product of AMPD2, inhibits aldolase B leading to increased fructose-1-phosphate. Hence, fructose metabolism is a mechanism for amplifying AMPD2 and blocking AMPD2 will be critical for blocking fructose mediated metabolic effects.

Example 9

Effects of IMP on Human Hepatocyte (HepG2) Cells

FIG. 17 shows that IMP, in concentrations of 1 to 100 µM, stimulates fat synthesis and blocks fat oxidation thus leading to fat accumulation. IMP, the product of AMP metabolism by AMPD2 is able to up-regulate fatty acid synthase (FAS) and AMPD2 expression with parallel down-regulation of the fat oxidation-associated protein Enoyl-CoA Hydratase (ECoAH). Allopurinol (AP) cannot fully rescue the reduction in ECoAH, consistent with IMP having direct effects to inhibit fat oxidation. IMP also stimulates triglyceride accumulation that is partially blocked by allopurinol. These studies show that the AMPD2 product, IMP, can stimulate fat accumulation by both stimulating fat synthesis and blocking fatty acid oxidation.

Discussion

The present inventors have found the importance of AMPD, in particular AMPD2, in driving obesity, fatty liver, kidney disease, pancreatic injury, diabetes, and other clinical conditions associated with metabolic syndrome. The present inventors have observed that activation of AMPD not only shunts AMP away from AMP activated protein kinase but also has direct effects to reduce ATP levels, stimulate fat synthesis, and block fat oxidation. This is believed to have downstream effects on insulin resistance, diabetes, hypertension, microvascular disease, systemic inflammation, endothelial function, oxidative stress, plasma triglycerides, HDL cholesterol, uric acid levels, weight, and chronic heart failure (SHF and DHF or HFpEF). Thus, various clinical conditions associated with metabolic syndrome can be treated by modulating, typically inhibiting, AMPD2 with or without blockade of the other AMPD isoforms. The AMPD2 inhibitor can also be used in combination with other drugs to potentiate its effects. This would include a wide variety of agents, including uric acid lowering drugs, AMP kinase stimulants, other agents used to treat diabetes including thioglitazones, antioxidants including ascorbate and resveratrol, and the catechins and flavenoids present in tea, cocoa and other nutrients.

It should be appreciated that the scope of the invention also includes various diagnostics, blood chemistry, and metabolites that can be used to identify AMPD2 inhibitors as well as identification and utilization of SNPs that indicate or contraindicate AMPD2 inhibitors, and identification and utilization of miRNA profiles that indicate or contraindicate AMPD2 inhibitors.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for treating a clinical condition associated with metabolic syndrome in a subject comprising administering to the subject in need of such a treatment a therapeutically effective amount of a composition comprising an adenosine monophosphate deaminase 2 (AMPD2) inhibitor, wherein said clinical condition is fatty liver, obesity or diabetes, or a combination thereof.

2. The method of claim 1, wherein the clinical condition associated with fatty liver comprises nonalcoholic fatty liver disease, nonalcoholic fatty liver disease associated cirrhosis, or a combination thereof.

3. The method of claim 1, wherein the composition reduces plasma triglycerides.

4. The method of claim 1, wherein the composition further comprises a xanthine oxidase inhibitor, a uricosuric agent, ketohexokinase (KHK) inhibitor, metformin, thiazolidinediones, an angiotensin-converting enzyme (ACE) inhibitor, an angiotensin receptor blocker, a thiazide diuretic, an antioxidant, catechin, resveratol, a uric acid lowering compound, or a combination thereof.

5. The method of claim 1, wherein the AMPD2 inhibitor inhibits expression of AMPD2 gene, enzymatic activity of AMPD2 enzyme, or a combination thereof.

6. The method of claim 5, wherein the AMPD2 inhibitor comprises a siRNA that inhibits expression of AMPD2 gene, an AMPD2 antibody, an AMP analog that inhibits AMPD2, an inhibitor of AMPDX that inhibits AMPD2, carbocyclic coformycin or a derivative thereof, carbocyclic nebularine or a derivative thereof, or deaminoformycin or a derivative thereof.

* * * * *

SEQUENCE LISTING

<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: shRNAmir

```
<400> SEQUENCE: 1
acctgggaat ctgctcattg tt                                          22
```